(12) United States Patent
Kim et al.

(10) Patent No.: US 9,261,586 B2
(45) Date of Patent: Feb. 16, 2016

(54) METHOD AND APPARATUS FOR GENERATING DIAGNOSIS IMAGE, DIAGNOSIS SYSTEM, AND MEDICAL IMAGE SYSTEM FOR PERFORMING THE METHOD

(75) Inventors: Kyu-hong Kim, Seongnam-si (KR); Sung-chan Park, Suwon-si (KR); Jung-ho Kim, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 71 days.

(21) Appl. No.: 13/447,638

(22) Filed: Apr. 16, 2012

(65) Prior Publication Data
US 2012/0271144 A1 Oct. 25, 2012

(30) Foreign Application Priority Data

Apr. 20, 2011 (KR) .................. 10-2011-0036846

(51) Int. Cl.
*G01S 7/52* (2006.01)
*A61B 8/08* (2006.01)
*A61B 8/00* (2006.01)
*G01S 15/89* (2006.01)

(52) U.S. Cl.
CPC ............... *G01S 7/52047* (2013.01); *A61B 8/00* (2013.01); *A61B 8/5207* (2013.01); *G01S 15/8997* (2013.01); *A61B 8/5246* (2013.01)

(58) Field of Classification Search
CPC ... G01S 15/8997; G01S 7/52047; A61B 8/00; A61B 8/5207; A61B 8/5246

USPC ............... 600/407, 437, 443; 382/128
See application file for complete search history.

(56) References Cited

U.S. PATENT DOCUMENTS

| | | | |
|---|---|---|---|
| 7,125,384 B2 | 10/2006 | Nishigaki et al. | |
| 8,666,197 B2 * | 3/2014 | Kim et al. | 382/299 |
| 2005/0043622 A1 * | 2/2005 | Jensen | 600/449 |
| 2010/0312112 A1 | 12/2010 | Kamiyama | |
| 2013/0258805 A1 * | 10/2013 | Hansen et al. | 367/8 |

FOREIGN PATENT DOCUMENTS

| | | |
|---|---|---|
| CN | 1646064 A | 7/2005 |
| CN | 101919707 A | 12/2010 |
| JP | 2009-240667 A | 10/2009 |
| KR | 10-2009-0042152 A | 4/2009 |

OTHER PUBLICATIONS

Synnevag et al., "Minimum variance adaptive beamforming applied to medical ultrasound imaging", IEEE Ultrasonics Symposium, 2005, pp. 1199-1202.*

(Continued)

*Primary Examiner* — Katherine Fernandez
(74) *Attorney, Agent, or Firm* — NSIP Law (57) ABSTRACT

A method of generating a diagnosis image includes receiving signals reflected from a subject; calculating a beamforming coefficient using the received signals; synthesizing each of the plurality of low resolution images using the calculated beamforming coefficient; and synthesizing a high resolution image using the synthesized plurality of low resolution images.

25 Claims, 6 Drawing Sheets

(56) References Cited

OTHER PUBLICATIONS

Holfort, Iben Kraglund, Fredrik Gran, and Jorgen Arendt Jensen. "Broadband minimum variance beamforming for ultrasound imaging." Ultrasonics, Ferroelectrics and Frequency Control, IEEE Transactions on 56.2 Feb. 2009: 314-325.

Holfort, Iben Kraglund, et al. "Adaptive receive and transmit apodization for synthetic aperture ultrasound imaging." Ultrasonics Symposium (IUS), 2009 IEEE International. Sep. 2009 (4 pages, in English).

Extended European Search Report mailed Feb. 5, 2014 in counterpart European Application No. 12 16 4935 (8 pages, in English).

Chinese Office Action issued on Jun. 8, 2015 in counterpart Chinese Application No. 201210105866.X (19 pages with English translation).

* cited by examiner

METHOD AND APPARATUS FOR GENERATING DIAGNOSIS IMAGE, DIAGNOSIS SYSTEM, AND MEDICAL IMAGE SYSTEM FOR PERFORMING THE METHOD

CROSS-REFERENCE TO RELATED APPLICATIONS

This application claims the benefit of Korean Patent Application No. 10-2011-0036846 filed on Apr. 20, 2011, in the Korean Intellectual Property Office, the disclosure of which is incorporated herein by reference in its entirety.

BACKGROUND

1. Field

This disclosure relates to a method and an apparatus for generating a diagnosis image, a diagnosis system, and a medical image system for performing the method.

2. Description of the Related Art

An image system using a synthetic aperture method may use a fixed beamforming method or an adaptive beamforming method. The fixed beamforming method uses a Hamming window or a Hann window regardless of an input signal, and is also referred to as a data-independent beamforming method. However, a diagnostic image generated according to the fixed beamforming method does not have a good contrast or a good resolution, and therefore the adaptive beamforming method may be used to obtain a high quality image. A diagnostic image generated according to the adaptive beamforming method has a high resolution, but is difficult to implement the adaptive beamforming method since data processing requirements are remarkably high.

SUMMARY

According to an aspect, a diagnosis image generation apparatus includes a beamforming coefficient calculation unit configured to calculate a beamforming coefficient to be used in common a plurality of low resolution images using signals reflected from a subject; a low resolution image synthesis unit configured to synthesize each of the plurality of low resolution images using the calculated beamforming coefficient; and a high resolution image synthesis unit configured to synthesize a high resolution image using the synthesized plurality of low resolution images.

The beamforming coefficient may be used in common to calculate a value at a same position in each of the plurality of low resolution images among values forming the plurality of low resolution images.

The beamforming coefficient calculation unit may be further configured to calculate the beamforming coefficient using a minimum variance (MV) beamforming technique for one of the plurality of low resolution images.

The one of the plurality of low resolution images may be one of the low resolution images that corresponds to a signal transmitted from a transducer that transmits the signal first in a transducer array, or a signal transmitted from a transducer that transmits the signal last in the transducer array, or a signal transmitted from a transducer that is located in a middle of the transducer array.

The beamforming coefficient calculation unit may be further configured to generate a covariance matrix for values forming one of the plurality of low resolution images; calculate an inverse of the generated covariance matrix; and calculate the beamforming coefficient to be used in common for the plurality of low resolution images using the calculated inverse of the covariance matrix.

The beamforming coefficient may vary depending on a value indicating a position of a value to which the beamforming coefficient is applied among values forming the plurality of low resolution images.

The image generation apparatus may further include an adaptive beamformer configured to form a reception beam used to output values forming the plurality of low resolution images using the calculated beamforming coefficient.

According to an aspect, a diagnosis system includes a probe configured to transmit/receive signals to/from a subject using a plurality of transducers; and a diagnosis image generation apparatus configured to synthesize each of a plurality of low resolution images to which a same beamforming coefficient is applied using the signals received by the probe; synthesize a high resolution image using the synthesized plurality of low resolution images; and output the synthesized high resolution image as a diagnosis image.

The transducers may be in a transducer array; and the one of the plurality of low resolution images may be one of the low resolution images that corresponds to a signal transmitted from one of the transducers that transmits the signal first in the transducer array, or a signal transmitted from one of the transducers that transmits the signal last in the transducer array, or a signal transmitted from one of the transducers that is located in a middle of the transducer array.

The diagnosis image generation apparatus may further include an adaptive beamformer configured to form a reception beam used to output values forming the plurality of low resolution images using the calculated beamforming coefficient as a beamforming weight.

According to an aspect, a medical image system includes a diagnosis system configured to synthesize each of a plurality of low resolution images to which a same beamforming coefficient is applied using signals reflected from a subject; synthesize a high resolution image using the synthesized plurality of low resolution images; and output the synthesized high resolution image as a diagnosis image. The medical image system further includes a display unit configured to display the output diagnosis image.

According to an aspect, a method of generating a diagnosis image includes receiving signals reflected from a subject; calculating a beamforming coefficient to be used in common for a plurality of low resolution images using the received signals; synthesizing each of the plurality of low resolution images using the calculated beamforming coefficient; and synthesizing a high resolution image using the synthesized plurality of low resolution images.

The calculating of the beamforming coefficient may include generating a covariance matrix for values forming one of the plurality of low resolution images; calculating an inverse of the generated covariance matrix; and calculating the beamforming coefficient to be used in common for the plurality of low resolution images using the calculated inverse of the covariance matrix.

According to an aspect, a non-transitory computer-readable storage medium stores a computer program for controlling a processor to perform the method described above.

According to an aspect, a method of generating a diagnosis image includes receiving signals reflected from a subject, the received signals including signals corresponding to a plurality of low resolution images of the subject; calculating a beamforming coefficient to be used in common for the plurality of low resolution images using signals corresponding to only one low resolution image of the plurality of low resolution images in the received signals; synthesizing each of the plurality of low resolution images using respective signals for each of the plurality of low resolution images in the received signals and the beamforming coefficient; and synthesizing a high resolution image using the plurality of synthesized low resolution images.

The signals corresponding to the plurality of low resolution images in the received signals may have been received at a plurality of reception points each corresponding to a different one of the plurality of low resolution images.

The synthesizing of each of the plurality of low resolution images may include using the beamforming coefficient to calculate a value at a same position in each of the plurality of low resolution images.

The beamforming coefficient may vary according to a position of a value in each of the plurality of low resolution images to which the beamforming coefficient is to be applied.

The calculating of the beamforming coefficient may include generating a covariance matrix of values of forming the one low resolution image using only the signals corresponding to the one low resolution image; calculating an inverse of the covariance matrix; and calculating the beamforming coefficient using the inverse of the covariance matrix.

Additional aspects will be set forth in part in the description that follows and, in part, will be apparent from the description, or may be learned by practice of the described examples.

BRIEF DESCRIPTION OF THE DRAWINGS

The above and/or other aspects will become apparent and more readily appreciated from the following description of examples, taken in conjunction with the accompanying drawings of which.

DETAILED DESCRIPTION

Reference will now be made in detail to examples that are illustrated in the accompanying drawings, wherein like reference numerals refer to like elements throughout. In this regard, these examples may have different forms and should not be construed as being limited to the descriptions set forth herein. Accordingly, the examples are merely described below by referring to the figures to explain aspects of the description.

Figure 1:
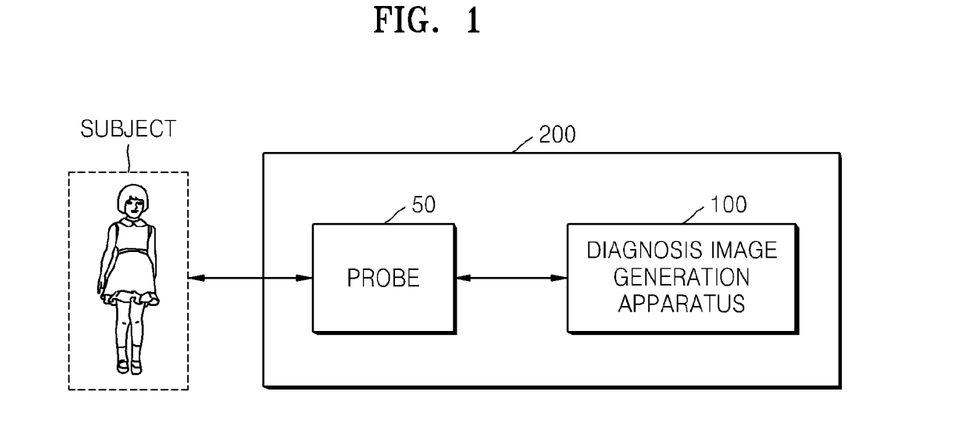
FIG. 1 is a diagram illustrating a use environment of a diagnosis system according to an example of the invention.

FIG. 1 is a diagram illustrating a use environment of a diagnosis system 200 according to an example of the invention. Referring to FIG. 1, the diagnosis system 200 includes a probe 50 and a diagnosis image generation apparatus 100. The diagnosis image generation apparatus 100 transmits/receives a signal to/from the probe 50, and generates a diagnosis image for a subject.

In greater detail, the probe 50 transmits a signal to the subject and receives a signal reflected from the subject with a plurality of transducers.

The diagnosis image generation apparatus 100 synthesizes each of a plurality of low resolution images by using signals received from the transducers, synthesizes a high resolution image by using the synthesized low resolution images, and generates a diagnosis image by using the synthesized high resolution image, according to a synthetic aperture method.

In this regard, the synthetic aperture method is a method in which one or more high resolution images are synthesized by synthesizing a plurality of low resolution images. A pixel value of a high resolution image may be set to the arithmetic mean of values forming low resolution images.

The values forming low resolution images according to this example may be information regarding a subject indicated by a signal reflected from the subject. In greater detail, since the absolute value of a magnitude of a signal reflected from the subject may indicate a brightness of the signal reflected from the subject, brightness information regarding the subject, according to this example, may be expressed as the magnitude of the signal reflected from the subject. Therefore, the values forming low resolution images may be the brightness information regarding the subject indicated by the signal reflected from the subject, or may be RF signals reflected from the subject.

In greater detail, a value at the same position of each low resolution image may be a value that indicates brightness information regarding the same point of the subject. In this case, since positions of transmission signals are not the same, the values that indicate brightness information regarding the same point of the subject and for the same position of each low resolution image may not be the same. That is, image sizes or received beamformed values with respect to the subject may not be the same.

Such a difference may be caused by a difference due to an offset according to where each of the transducers transmits a signal to the subject. That is, when each transducer transmits a signal to the subject, an offset according to where each of transducers in different positions transmits a signal for the subject occurs, and thus a difference occurs between values for the same position of each low resolution image or between received RF signal values. Therefore, the synthetic aperture method reciprocally compensates for the difference between received signals at the same location of the subject to synthesize a high resolution image.

The diagnosis image generation apparatus 100 according to this example uses a same beamforming coefficient to synthesize a plurality of low resolution images. The beamforming coefficient may be a beamforming weight.

Accordingly, the diagnosis image generation apparatus 100 may reduce the number of operations required to synthesize the plurality of low resolution images and generate a high definition diagnosis image for a subject.

Figure 2:
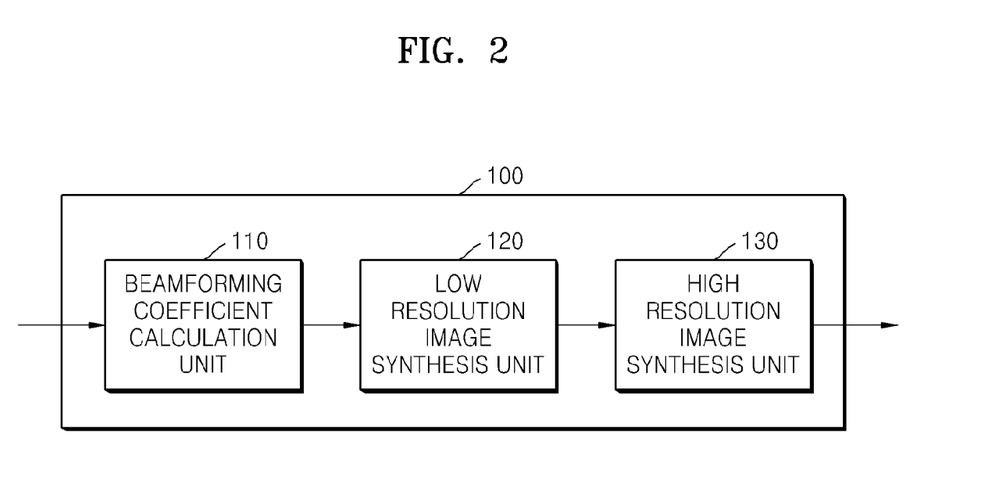
FIG. 2 is a block diagram illustrating a diagnosis image generation apparatus of FIG. 1 according to an example of the invention.

FIG. 2 is a block diagram illustrating the diagnosis image generation apparatus 100 of FIG. 1 according to an example of the invention. Referring to FIG. 2, the diagnosis image generation apparatus 100 includes a beamforming coefficient calculation unit 110, a low resolution image synthesis unit 120, and a high resolution image synthesis unit 130.

In the diagnosis image generation apparatus 100 of FIG. 2, only elements associated with this example are illustrated. Therefore, those skilled in the art will understand that the diagnosis image generation apparatus 100 may also include other elements in addition to the elements in FIG. 2.

Further, the beamforming coefficient calculation unit 110, the low resolution image synthesis unit 120, and the high resolution image synthesis unit 130 of the diagnosis image generation apparatus 100 of FIG. 2 may correspond to one or more processors. The processor may be implemented with an array of logic gates, or may be implemented with a combination of a general microprocessor and a memory storing a program executable by the microprocessor. Also, those skilled in the art will understand that the elements of the diagnosis image generation apparatus 100 may be implemented with other types of hardware.

The diagnosis image generation apparatus 100 may generate a high resolution image for a subject, and the generated high resolution image may be a diagnosis image of the subject.

The beamforming coefficient calculation unit 110 calculates a beamforming coefficient that is to be used in common for a plurality of low resolution images by using a signal reflected from the subject. In this regard, the beamforming coefficient may be referred as a beamforming weight of a beamformer, and the calculated beamforming coefficient may be used to calculate values forming the low resolution images.

Accordingly, the beamforming coefficient calculated by the beamforming coefficient calculation unit 110 is used in common to calculate a reception signal value for the same position of the low resolution images among the values forming the low resolution images.

For example, when first through third low resolution images are used, the low resolution image synthesis unit 120 uses the same beamforming coefficient to calculate a first reception signal value at a position (a, b) among reception signal values forming the first low resolution image, a second reception signal value at a position (a, b) among reception signal values forming the second low resolution image, and a third reception signal value at a position (a, b) among reception signal values forming the third low resolution image.

In greater detail, the beamforming coefficient of the diagnosis image generation apparatus 100 according to this example is a coefficient used to calculate values forming a diagnosis image in the low resolution image synthesis unit 120. In this regard, when the beamforming coefficient according to this example is used to calculate the values forming the low resolution image, an input/output gain of a signal received in an orientation direction is 1 among signals received by a plurality of transducers, and the signals received by the transducers have the minimum output power. For example, the orientation direction may include a direction of arrival (DOA), but the orientation direction is not limited thereto.

That is, the transducers receive signals reflected from the subject. In this regard, a phase difference occurs with respect to the signal received by each transducer by due to a delay time due to incidence angles of the signals received by the transducers, and is used to calculate the beamforming coefficient.

For example, the beamforming coefficient calculation unit 110 according to this example may calculate the beamforming coefficient by using a technique used in a minimum variance (MV) beamformer.

More specifically, when the diagnosis image generation apparatus 100 uses I low resolution images, the beamforming coefficient calculation unit 110 calculates one beamforming coefficient that is to be used in common for the I low resolution images by using a MV technique. The MV technique is a method of calculating the beamforming coefficient that allows a variance value of a beamforming result to be minimized without distortion of a target direction in performing beamforming.

When a signal transmitted/received between the subject and the transducers is an ultrasonic signal, if a signal having a large value injected to an off-axis side is not included in signals received by the diagnosis image generation apparatus 100, the MV technique may considered to have a physical meaning in that the beamforming result is not greatly influenced although a sidelobe beam increases. Thus, assuming that there is no big path change in a propagation of ultrasound between values forming a plurality of low resolution images and indicating the same position, although the low resolution images share the beamforming coefficient, the beamforming result is little influenced by such sharing.

Accordingly, the beamforming coefficient calculation unit 110 calculates the beamforming coefficient by using the MV technique to form one of the I low resolution images. In this regard, the beamforming coefficient corresponding to each space position may be used in common for the I low resolution images. In greater detail, the beamforming coefficient calculation unit 110 may calculate beamforming coefficients with respect to all values forming one low resolution image, and use the calculated beamforming coefficients in common for the values forming each of the I low resolution images.

The beamforming coefficient calculation unit 110 may select one low resolution image from the I low resolution images in various ways in calculating beamforming coefficients of the selected low resolution image.

For example, the beamforming coefficient calculation unit 110 may select one low resolution image according to a signal transmitted from a transducer that transmits the signal first among a transducer array, one low resolution image according to a signal transmitted from a transducer that transmits the signal last among the transducer array, or one low resolution image according to a signal transmitted from a transducer that is located in the middle of the transducer array, but the method of selecting the one low resolution image is not limited thereto. This will be described in greater detail with reference to FIG. 3 below.

As an example of a method of calculating the beamforming coefficients in the beamforming coefficient calculation unit 110, the beamforming coefficient calculation unit 110 may generate a covariance matrix with respect to values forming one of a plurality of low resolution images, calculate an inverse of the covariance matrix, and calculate a beamforming coefficient to be used in common for the low resolution images by using the inverse of the covariance matrix.

In greater detail, the beamforming coefficient calculation unit 110 may generate a covariance matrix with respect to values forming one low resolution image, calculate an inverse of the covariance matrix, and calculate a beamforming coefficient to be used in common for the low resolution images by using the inverse of the covariance matrix and a steering vector with respect to signals received by transducers after a signal is transmitted from a transducer and is reflected from a subject.

For example, the covariance matrix may be calculated from a signal received by a transducer and an expectation value of a Hermitian transpose with respect to the signals received by the transducer.

That is, the beamforming coefficient calculation unit 110 may perform operations expressed by Equations 1 and 2 below to calculate a beamforming coefficient w.

$$w = \frac{\hat{R}^{-1} e}{e^H \hat{R}^{-1} e} \quad (1)$$

where w denotes the beamforming coefficient for one low resolution image, e denotes a steering vector, $e^H$ denotes a Hermitian transpose of the steering vector, and $\hat{R}^{-1}$ is the inverse of a covariance matrix for one low resolution image.

In greater detail, the steering vector e is for controlling a phase of a signal that is transmitted from a probe (not shown) to a subject. When it is assumed that a time delay value for beamforming has been applied beforehand according to a direction, the steering vector is set to 1 because a beamforming coefficient is a real value.

Further, a covariance $R(\vec{r}_p)$ according to this example may be expressed as Equation 2 below, $$R(\vec{r}_p) = E\{y_i(\vec{r}_p) y_i(\vec{r}_p)^H\} \quad (2)$$

where $\vec{R}_p$ denotes a focal point of the signal reflected from the subject, $R(\vec{r}_p)$ denotes a covariance for a value in a position $\vec{r}_p$, $E\{\}$ denotes an expectation value, $y_i()$ denotes a signal received for an i-th low resolution image, and $y_i()^H$ denotes a Hermitian transpose of $y_i()$.

Those skilled in the art will recognize that a sample variance calculation method, a sub-array method, a diagonal loading method, etc., may be used to specify Equations 1 and 2 above.

Therefore, the beamforming coefficient calculation unit 110 generates a covariance matrix according to Equation 2 above with respect to values forming one low resolution image, calculates an inverse of the covariance matrix, and calculates a beamforming coefficient by using the inverse of the covariance matrix and a steering vector according to Equation 1 above.

The beamforming coefficient calculation unit 110 may also calculate an inverse of a covariance $\hat{R}^{-1}$ having increased stability by using a diagonal loading method for ensuring stability in calculating the inverse of the covariance matrix.

Therefore, the beamforming coefficient calculation unit 110 performs the operations described above to calculate a beamforming coefficient to be used in common for a plurality of low resolution images. That is, the beamforming coefficient calculated by the beamforming coefficient calculation unit 110 may be an m×n matrix, and a beamforming weight at a position (m, n) may be used in common for a value for the position (m, n) among values forming the low resolution images.

The method described above is merely one example of the invention of calculating a beamforming coefficient of an adaptive beamformer, and the invention is not limited thereto.

Accordingly, the beamforming coefficient calculation unit 110 may calculate the beamforming coefficient to be used in common for the low resolution images by using any of a variety of methods.

The low resolution image synthesis unit 120 synthesizes each of a plurality of low resolution images using the beamforming coefficient calculated by the beamforming coefficient calculation unit 110. The synthesizing of a low resolution image by the low resolution image synthesis unit 120 may be the generating of the low resolution image as well as the generating of values forming the low resolution image.

The low resolution image synthesis unit 120 according to this example may include a beamformer (not shown), and may synthesize each of a plurality of low resolution images by using a signal outputted from the beamformer. In this regard, the beamformer according to this example may be an adaptive beamformer that forms a reception beam for outputting values forming the low resolution image, but is not limited thereto.

As an example where M transducers receive a signal reflected from a subject, values output by the low resolution image synthesis unit 120 may be expressed by the following Equation 3:

$$\hat{b}_i(\vec{r}_p) = \sum_{m=0}^{M-1} w_m^*(\vec{r}_p) y_{m,i}(\Delta_{m,i}(\vec{r}_p)) \quad (3)$$

where $\vec{r}_p$ denotes a focal point of a signal reflected from the subject, $\hat{b}_i(\vec{r}_p)$ denotes a value of a received signal reflected from a position $\vec{r}_p$ among values forming an i-th low resolution image, $w_m^*(\vec{r}_p)$ denotes a beamforming coefficient for a value of a signal in the position $\vec{r}_p$ among values of the received signal forming one of the low resolution images based on a signal received by an m-th transducer, a superscript * denotes a conjugate complex, $y_{m,i}()$ denotes a value of a signal received by the m-th transducer for forming values of the i-th low resolution image, $\Delta_{m,i}$ denotes a sampling time for signals received by the m-th transducer for the i-th low resolution image, and $y_{m,i}(\Delta_{m,i}(\vec{r}_p))$ denotes a value of a signal that is obtained by applying a delay value in the position $\vec{r}_p$ for a signal received by the m-th transducer for the i-th low resolution image.

Therefore, the low resolution image synthesis unit 120 performs an operation according to Equation 3 to synthesize a plurality of low resolution images by using signals that are respectively received by the M transducers.

In this regard, the beamforming coefficient $w_m^*(\vec{r}_p)$ calculated by the beamforming coefficient calculation unit 110 does not have i as a parameter because the beamforming coefficient of this example is used in common for the plurality of low resolution images.

As described above, although the beamforming coefficient $w_m^*(\vec{r}_p)$ does not have i as a parameter, the beamforming coefficient $w_m^*(\vec{r}_p)$ has $\vec{r}_p$ indicating a focal point of a signal reflected from a subject and m indicating a transducer that receives a signal among a plurality of transducers as parameters. Therefore, the beamforming coefficient $w_m^*(\vec{r}_p)$ may vary depending on a value indicating a position of a value to which the beamforming coefficient is applied among the values forming the low resolution image.

Accordingly, the beamforming coefficient $w_m^*(\vec{r}_p)$ of this example is applied to the spatially same position, and thus the number of operations performed by the diagnosis image generation apparatus 100 may be considerably reduced, and moreover, the quality of the generated diagnosis image in terms of contrast and resolution may be ensured.

Like the calculation of the beamforming coefficient by using the covariance matrix as described above, the operation of calculating the inverse of the covariance matrix to calculate the beamforming coefficient accounts for a majority of the operations performed by the diagnosis image generation apparatus 100. In greater detail, an adaptive beamformer requires a number of operations approximately equal to the number of ultrasound reception channels raised to the power of 3 to calculate the beamforming coefficient.

Accordingly, when the beamforming coefficient calculated by the beamforming coefficient calculation unit 110 of this example is used in common for the plurality of low resolution images, the number of operations performed by the diagnosis image generation apparatus 100 is considerably reduced, and thus the performance thereof is enhanced.

The high resolution image synthesis unit 130 synthesizes high resolution images by using the synthesized low resolution images. For example, the high resolution image synthesis unit 130 performs an operation of generating one or more high resolution image signals by averaging the low resolution image signals synthesized by the low resolution image synthesis unit 120.

For an example of transmitting a signal from the transducers to the subject I times, an operation performed by the high resolution image synthesis unit 130 may be expressed by the following Equation 4:

$$\hat{b}(\vec{r}_p) = \frac{1}{I}\sum_{i=o}^{I-1} \hat{b}_i(\vec{r}_p) \qquad (4)$$

where $\hat{b}(\vec{r}_p)$ denotes a value indicating a brightness in a position $\vec{r}_p$ among values forming a high resolution image, I denotes the number of low resolution images, and $\hat{b}_i(\vec{r}_p)$ denotes a value of the position $\vec{r}_p$ among the values forming the i-th low resolution image calculated using Equation 3.

That is, the high resolution image synthesis unit 130 outputs high resolution images by synthesizing I low resolution images by performing the operation described by Equation 4.

The high resolution images synthesized by the high resolution image synthesis unit 130 of this example may be generated as diagnosis images. Accordingly, the diagnosis image generation apparatus 100 may considerably reduce the number of operations required to generate a diagnosis image, and moreover, may generate a high definition diagnosis image.

Figure 3:
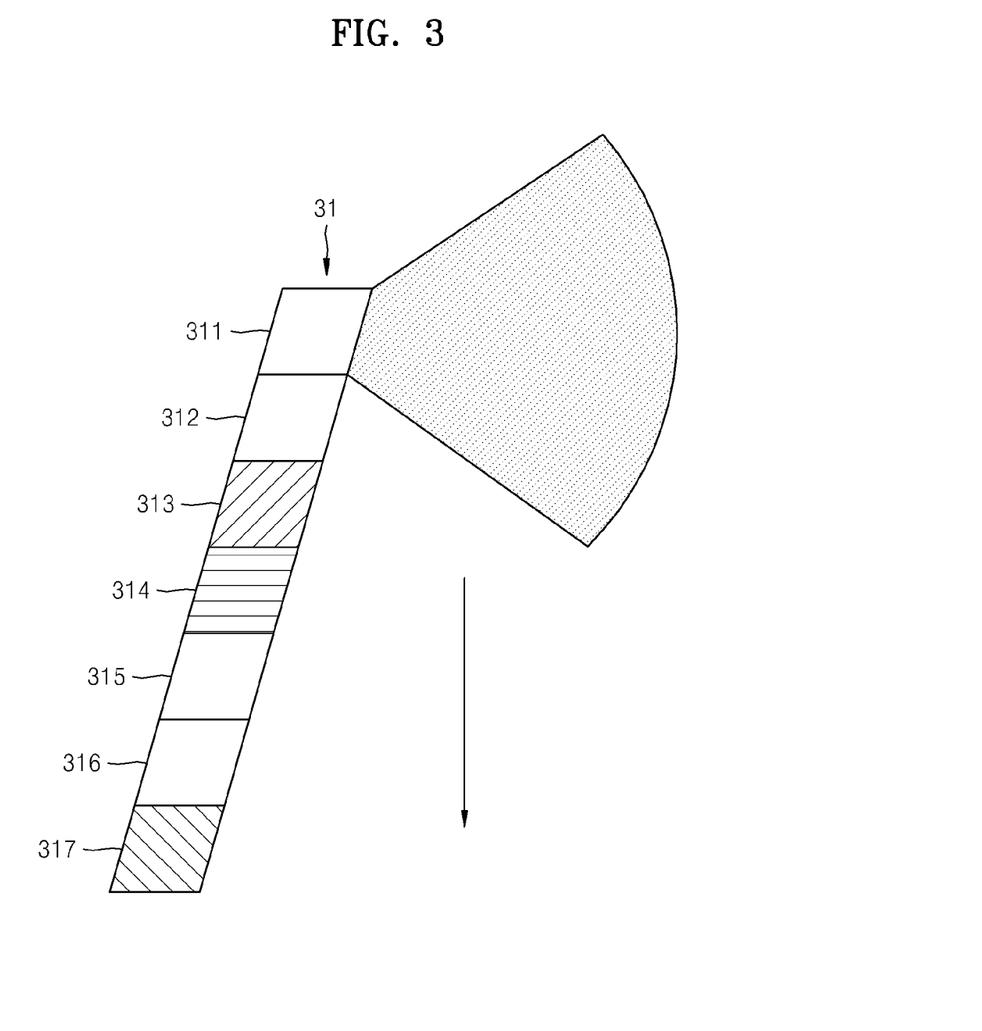
FIG. 3 is a diagram illustrating a method of selecting one of a plurality of low resolution images in a beamforming coefficient calculation unit of FIG. 2 according to an example of the invention.

FIG. 3 is a diagram illustrating a method of selecting one of a plurality of low resolution images in the beamforming coefficient calculation unit 110 of FIG. 2 according to an example of the invention. Referring to FIGS. 2 and 3, a line of a transducer array 31 is shown. For convenience of description, a signal will be assumed to be transmitted to a subject sequentially from a transducer 311 to a transducer 317 that are included in the transducer array 31, but the invention is not limited to this manner of operation of the transducer array 31. For example, sub arrays may be formed by two or more transducers included in the transducer array 31, may overlap each other, and may sequentially transmit a signal to a subject.

As an example of the method of selecting one of the low resolution images, the beamforming coefficient calculation unit 110 may select the low resolution image according to a signal transmitted from the transducer 311 that transmits the signal first among the transducers 311 through 317 of the transducer array 31, and may calculate a beamforming coefficient to be used in common for the low resolution images using the signal transmitted from the transducer 311.

As another example, the beamforming coefficient calculation unit 110 may select the low resolution image according to a signal transmitted from the transducer 317 that transmits the signal last among the transducers 311 through 317 of the transducer array 31, and may calculate the beamforming coefficient to be used in common for the low resolution images using the signal transmitted from the transducer 317.

As another example, the beamforming coefficient calculation unit 110 may select the low resolution image according to a signal transmitted from the transducer 314 located in the middle of the transducer array 31, and may calculate a beamforming coefficient to be used in common for the low resolution images using the signal transmitted from the transducer 314.

The methods described above are merely examples of selecting one of the low resolution images to calculate a beamforming coefficient to be used in common for the low resolution images in the beamforming coefficient calculation unit 110, and the invention is not limited to these examples. For example, one of the low resolution images may be selected by using various other methods, including selecting one of the low resolution images at random.

Accordingly, the beamforming coefficient calculation unit 110 selects one of a plurality of low resolution images, and calculates a beamforming coefficient to be used in common for the low resolution images.

Figure 4:
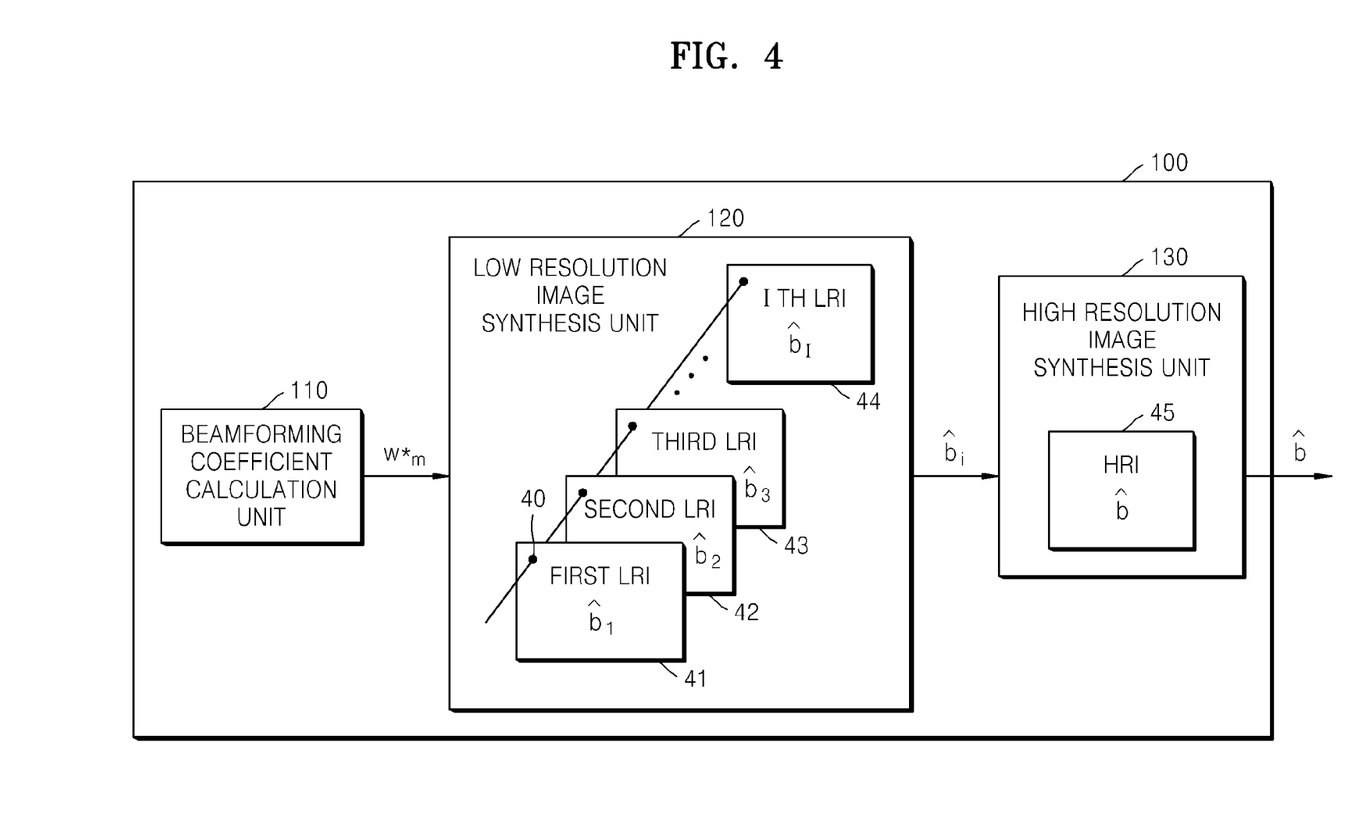
FIG. 4 is a diagram illustrating a method of synthesizing low resolution images and a high resolution image by using a beamforming coefficient calculated by the beamforming coefficient calculation unit of FIG. 2 according to an example of the invention.

FIG. 4 is a diagram illustrating a method of synthesizing low resolution images and a high resolution image by using a beamforming coefficient calculated by the beamforming coefficient calculation unit 110 of FIG. 2 according to this example. For convenience of description, the diagnosis image generation apparatus 100 will be assumed to transmit and receive a signal to and from a subject I times by using M transducers included in the probe 50, but the invention is not limited to this manner of operation.

Those skilled in the art will recognize that I low resolution images may be synthesized because the M transducers may transmit and receive the signal to and from the subject I times.

Referring to FIGS. 2 and 4, the beamforming coefficient calculated by the beamforming coefficient calculation unit 110 is $w_m^*$. In this regard, m denotes an m-th transducer among the M transducers, and thus $w_m^*$ denotes the beamforming coefficient for a signal received by the m-th transducer.

In greater detail, the beamforming coefficient calculation unit 110 calculates the beamforming coefficient to be used in common for a plurality of low resolution images. In this regard, the beamforming coefficient may be calculated by using a MV technique for one of a plurality of low resolution images.

For convenience of description, the I low resolution images of the low resolution image synthesis unit 120 will be assumed as an image type, but the invention is not limited to this. In greater detail, it will be assumed that values forming a low resolution image indicate brightness values of pixels included in low resolution images, but the invention is not limited to this.

The beamforming coefficient calculated by the beamforming coefficient calculation unit 110 is $w_m^*(\vec{r}_p)$, which denotes a beamforming coefficient for a pixel at a position $\vec{r}_p$ among pixels forming one low resolution image according to the signal received by the m-th transducer.

The low resolution image synthesis unit 120 performs an operation of synthesizing each of a plurality of low resolution images by using the beamforming coefficient $w_m^*$ calculated by the beamforming coefficient calculation unit 110. Accordingly, the low resolution image synthesis unit 120 outputs the plurality of low resolution images, which are denoted by $\hat{b}_i$.

As an example of synthesizing the I low resolution images, $\hat{b}_1$ denotes a first low resolution image 41, $\hat{b}_2$ denotes a second low resolution image 42, $\hat{b}_3$ denotes a third low resolution image 43, and $\hat{b}_I$ denotes an I-th low resolution image 44.

A pixel value indicating the low resolution images output by the low resolution image synthesis unit 120 may be $\hat{b}_i(\vec{r}_p)$ in terms of a pixel unit. That is, $\hat{b}_i(\vec{r}_p)$ denotes a pixel value for a pixel of the position $\vec{r}_p$ among pixels forming the I-th low resolution image.

In greater detail, the same beamforming coefficient is used for pixels 40 at the same position in each of the low resolution images among pixels forming the low resolution images.

The high resolution image synthesis unit 130 performs an operation of synthesizing high resolution images by using the low resolution images $\hat{b}_i$ output by the low resolution image synthesis unit 120. Accordingly, the high resolution image synthesis unit 130 outputs a high resolution image 45, which is denoted by $\hat{b}$.

A pixel value of the high resolution image $\hat{b}$ output by the high resolution image synthesis unit 130 may be $\hat{b}(\vec{r}_p)$ in terms of a pixel unit. That is, $\hat{b}(\vec{r}_p)$ denotes a pixel value for a pixel at the position $\vec{r}_p$ among pixels forming the high resolution image $\hat{b}$.

Accordingly, the diagnosis image generation apparatus 100 of this example synthesizes a plurality of low resolution images and a high resolution image by using one beamforming coefficient, thereby considerably reducing the number of operations required to synthesize the plurality of low resolution images, and also generating a high definition diagnosis image.

Figure 5:
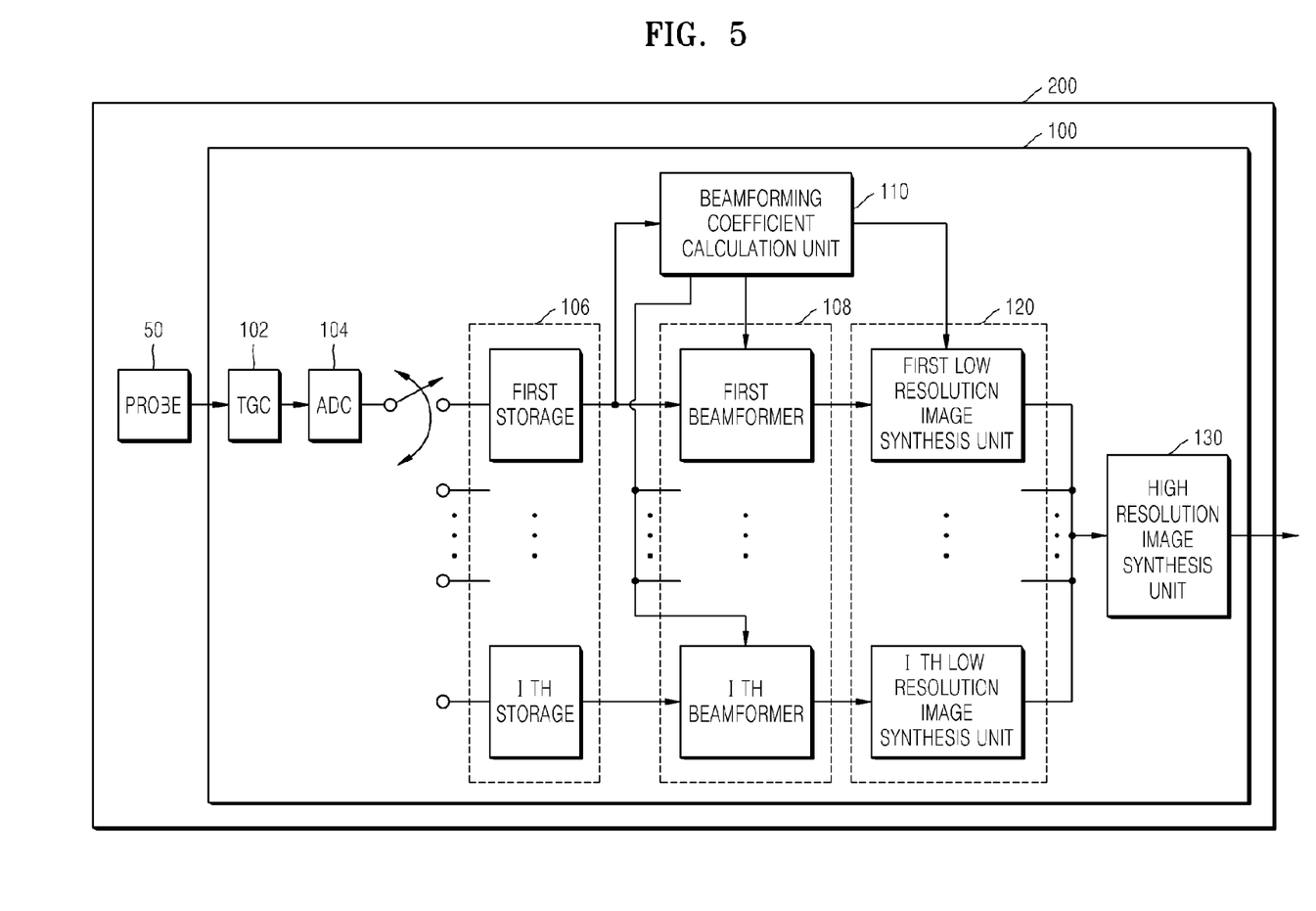
FIG. 5 is a block diagram illustrating a diagnosis system according to an example of the invention.

FIG. 5 is a block diagram illustrating a diagnosis system 200 according to an example of the invention. The diagnosis system 200 includes the probe 50 and the diagnosis image generation apparatus 100. The diagnosis image generation apparatus 100 includes a time gain compensation (TGC) circuit 102, an analog-to-digital converter (ADC) 104, a storage unit 106, the beamforming coefficient calculation unit 110, a beamformer 108, the low resolution image synthesis unit 120, and the high resolution image synthesis unit 130. The storage unit 106 may include first to I-th storages, the beamformer 108 may include first to I-th beamformers, and the low resolution image synthesis unit 120 may include first to I-th low resolution image synthesis units.

In FIG. 5, although the beamformer 108 is separated from the low resolution image synthesis unit 120, the invention is not limited to this arrangement, and those skilled in the art will recognize that the beamformer 108 may be included in the low resolution image synthesis unit 120.

For convenience of description, in FIG. 5, a signal is transmitted/received between the probe 50 and a subject I times, and accordingly values forming I low resolution images are generated, but those skilled in the art will recognize that the invention is not limited to this manner of operation.

The diagnosis system 200 of FIG. 5 illustrates only elements related to an example of the invention. Therefore, those skilled in the art will recognize that the diagnosis system 200 may also include other elements in addition to the elements in FIG. 5.

The diagnosis image generation apparatus 100 of FIG. 5 is an example of the diagnosis image generation apparatus 100 of FIGS. 1 and 2. However, the diagnosis image generation apparatus 100 of FIGS. 1 and 2 is not limited to the elements in FIG. 5. Also, the description associated with FIGS. 1 to 4 is also applicable to the diagnosis image generation apparatus 100 of FIG. 5, and accordingly that description will not be repeated here for conciseness.

In the diagnosis system 200 according to this example, the diagnosis image generation apparatus 100 generates a diagnosis image for a subject by using a signal transmitted/received between the subject and the probe 50. In this regard, the signal transmitted/received between the subject and the probe 50 may be an ultrasonic signal and a diagnosis image of the subject may be an ultrasonic image, but the invention is not limited an ultrasonic implementation.

The probe 50 transmits/receives a signal to/from the subject with a plurality of transducers. In this regard, the transducers may be a transducer array. When a signal transmitted/received by the probe 50 is an ultrasonic signal, each of the transducers in the probe 50 converts an electric signal into an ultrasonic signal, transmits the ultrasonic signal to the subject, receives an ultrasonic signal reflected by the subject, and converts the received ultrasonic signal into an electric signal.

Using signals received by the probe 50, the diagnosis image generation apparatus 100 synthesizes each of a plurality of low resolution images to which the same beamforming coefficient is applied, synthesizes a high resolution image by using the synthesized low resolution images, and outputs the synthesized high resolution image as a diagnosis image.

The TGC circuit 102 compensates a signal received from the probe 50 for signal attenuation based on depth. In greater detail, when a signal transmitted/received by the probe 50 is an ultrasonic signal, an ultrasonic beam has a characteristic where the ultrasonic beam attenuated in a subject according to a depth. Therefore, a signal reflected from a part of the subject that is far away from a surface of the probe 50 is relatively weaker than a signal reflected from a part of the subject that is close to the surface of the probe 50, so that an image based on the signal reflected from the part far away from the surface of the probe 50 is displayed darker than an image based on the signal reflected from the part close to the surface of the probe 50. Accordingly, the TGC circuit 102 compensates for signal attenuation due to a depth and thus allows signals reflected from different parts of the subject at different depths to be displayed at the same brightness. TGC is well known in the art, and accordingly will not be described in further detail for conciseness.

The ADC 104 converts a signal that has compensated by the TGC circuit 102 into a digital signal.

The storage unit 106 stores the digital signal that has been converted by the ADC 104. In this regard, the storage unit 106 according to this example may include the first to I-th storages.

In greater detail, when the transducers included in the array transducer sequentially transmit a signal, first, the first transducer of the transducers transmits a signal to the subject, and each of the transducers receives a signal reflected from the subject. The received signals are stored in the first storage of the storage unit 106 through the TGC circuit 102 and the ADC 104.

Second, the second transducer of the transducers transmits a signal to the subject, and each of the transducers receives a signal reflected from the subject. The received signals are stored in the second storage (not shown) of the storage unit 106 through the TGC circuit 102 and the ADC 104.

This same process is repeated in order for each of the remaining transducers until the I-th transducer of the transducers transmits a signal to the subject, and each of the transducers receives a signal reflected from the subject. The received signals are stored in the I-th storage of the storage unit 106 through the TGC 102 circuit and ADC 104.

Those skilled in the art will recognize that the storage unit 106 as a general storage medium may include a hard disk drive (HDD), a read only memory (ROM), a random access memory (RAM), a flash memory, a memory card, or any other suitable storage medium that is known in the art.

The beamforming coefficient calculation unit 110 calculates a beamforming coefficient to be used in common for the plurality of low resolution images by using data of the received signals stored in the storage unit 106. In this regard, the beamforming coefficient calculation unit 110 calculates the beamforming coefficient by using data stored in a selected one of the first through I-th storages of the storage unit 106, i.e., by using data corresponding to one low resolution image selected from I low resolution images.

For convenience of description, although the beamforming coefficient may be calculated by using data stored in the first storage of the storage unit 106 in FIG. 5, the invention is not limited thereto, and the beamforming coefficient may be calculated by using data stored in any of the storages of the storage unit 106 by using the variety of methods described with respect to FIG. 3.

The beamformer 108 and the low resolution image synthesis unit 120 synthesize each of a plurality of low resolution images by using the beamforming coefficient calculated by the beamforming efficient calculation unit 110. In this regard, the beamformer 108 may include the first to I-th beamformers, and the low resolution image synthesis unit 120 may include the first to I-th low resolution image synthesis units. The first to I-th beamformers and the first to I-th low resolution image synthesis units may respectively use the data stored in the first through I-th storages and output values forming each of the plurality of low resolution images to which the beamforming coefficient calculated by the beamforming coefficient calculation unit 110 is applied.

The high resolution image synthesis unit 130 synthesizes the high resolution image by using the low resolution images synthesized by the low resolution image synthesis unit 120.

In the above description, the storage unit 106, the beamformer 108, and the low resolution image synthesis unit 120 may be included in one hardware unit, or may provided as separate hardware units. Also, the first to I-th storages, the first to I-th beamformers, and the first to I-th low resolution image synthesis units may be included in respective virtual spaces divided in one hardware unit, or may be included in respective physical spaces divided in one hardware unit, or may be provided as separate hardware units.

However, the invention is not limited to these configurations. Those skilled in the art will recognize that the storage unit 106, the beamformer 108, and the low resolution image synthesis unit 120 may be included in a plurality of hardware units that respectively correspond to the first to I-th storages, the first to I-th beamformers, and the first to I-th low resolution image synthesizers, respectively.

As described above, the diagnosis image generation apparatus 100 according to this example synthesizes a plurality of low resolution images by using one beamforming coefficient calculated by the beamforming coefficient calculation unit 110 in common, thereby considerably reducing the number of operations performed by the diagnosis image generation apparatus 100, and ensuring the quality of the generated high resolution image.

Figure 6:
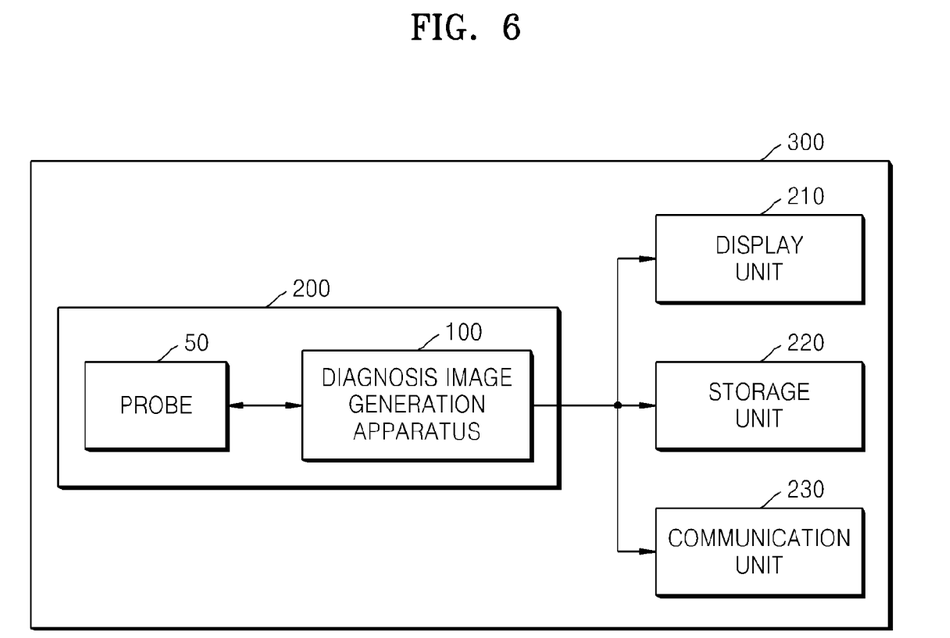
FIG. 6 is a block diagram illustrating a medical image system according to an example of the invention.

FIG. 6 is a block diagram illustrating a medical image system 300 according to an example of the invention. Referring to FIG. 6, the medical image system 300 according to this example includes the diagnosis system 200, a display unit 210, a storage unit 220, and a communication unit 230. The diagnosis system 200 includes the probe 50 and the diagnosis image generation apparatus 100.

In the medical image system 300 of FIG. 6, only elements associated with this example are illustrated. Therefore, those skilled in the art will recognize that the medical image system 300 may also include other elements in addition to the elements in FIG. 6.

The probe 50, the diagnosis image generation apparatus 100 and the diagnosis system 200 of FIG. 6 may correspond to the examples of the probe 50, the diagnosis image generation apparatus 100, and the diagnosis system 200 of FIGS. 1, 2, and 5. Accordingly, the description associated with FIGS. 1 to 5 is also applicable to the medical image system 300 of FIG. 6, and accordingly that description will not be repeated here for conciseness.

The diagnosis system 200 synthesizes each of a plurality of low resolution images to which the same beamforming coefficient is applied using signals received from the transducers, synthesizes a high resolution image by using the synthesized low resolution images, and outputs the synthesized high resolution image as a diagnosis image.

Therefore, the probe 50 transmits/receives a signal to/from a subject using the transducers. The diagnosis image generation apparatus 100 synthesizes each of a plurality of low resolution images to which the same beamforming coefficient is applied using signals received from the probe 50, synthesizes a high resolution image using the synthesized low resolution images, and outputs the synthesized high resolution image as a diagnosis image.

The display unit 210 displays the diagnosis image outputted from the diagnosis system 200. For example, the display unit 210 may include output devices such as a display panel, a touch screen, and a monitor that are included in the medical image system 300, and a plurality of software modules for respectively driving the output devices.

The storage unit 220 stores the diagnosis image outputted from the diagnosis system 200. For example, those skilled in the art will recognize that the storage unit 220 as a general storage medium may include a HDD, a ROM, a RAM, a flash memory, a memory card, or any other suitable storage medium that is known in the art.

The communication unit 230 transmits the diagnosis image outputted from the diagnosis system 200 to an external device (not shown) and receives data from the external device. In this regard, the external device may be a fax machine, a general computer system, or another medical image system that is disposed at a remote location.

The communication unit 230 may transmit/receive data to/from the external device over a wired/wireless network. Examples of the network include the Internet, a local area network (LAN), a wireless LAN, a wide area network (WAN), and a personal area network (PAN), but it is not limited to these examples. The network may be any suitable type of network for transmitting/receiving information that is known in the art.

Moreover, those skilled in the art will recognize that the storage unit 220 and the communication unit 230 may be integrated in a device such as a picture archiving and communication system (PACS) by adding an image reading function and a search function.

Therefore, the medical image system 300 may display, store, and transmit a diagnosis image that is generated and outputted by the diagnosis image generation apparatus 200.

Figure 7:
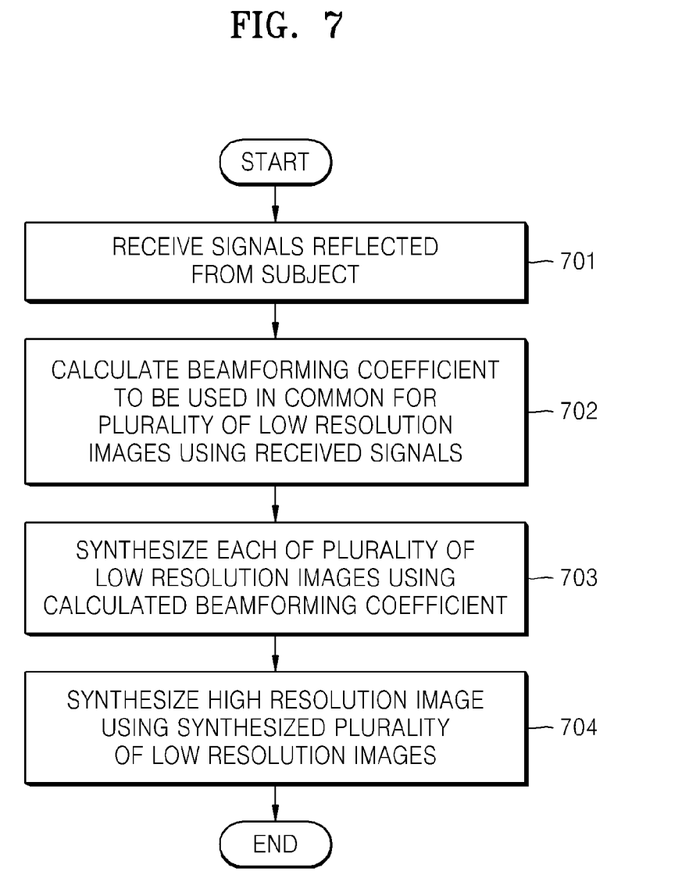
FIG. 7 is a flowchart illustrating a method of generating a diagnosis image according to an example of the invention.

FIG. 7 is a flowchart illustrating a method of generating a diagnosis image according to an example of the invention. Referring to FIG. 7, the method includes a plurality of operations that are sequentially processed in the probe 50, the diagnosis image generation apparatus 100, and the medical image system 300 of FIGS. 1, 2, 5, and 6. Therefore, the descriptions associated with the probe 50, the diagnosis image generation apparatus 100, and the medical image system 300 of FIGS. 1, 2, 5, and 6 apply to the method of FIG. 7, and accordingly those descriptions will not be repeated here for conciseness.

In operation 701, the probe 50 receives signals reflected from a subject. In this regard, the signal reflected from the subject is a signal that is transmitted by the probe 50 and reflected from the subject.

In operation 702, the beamforming coefficient calculation unit 110 calculates a beamforming coefficient to be used in common for a plurality of low resolution images using the signals received in operation 701 for one of the low resolution images.

In operation 703, the low resolution image synthesis unit 120 synthesizes each of a plurality of low resolution images using the signals received in operation 701 for respective ones of the low resolution images and the beamforming coefficient calculated in operation 702.

In operation 704, the high resolution image synthesis unit 130 synthesizes a high resolution image using the low resolution images synthesized in operation 703. Accordingly, the synthesized high resolution image may be generated and outputted as a diagnosis image.

Therefore, the diagnosis image generation apparatus 100 according to this example uses a beamforming coefficient in common for a plurality of the low resolution images. Therefore, the number of operations required to synthesize the plurality of low resolution images is may be considerably reduced, and the quality of a high resolution image may be ensured.

For example, when a high resolution image is synthesized by using 64 low resolution images by using a synthetic aperture method, if the diagnosis image generation apparatus 100 according to this example uses a beamforming coefficient in common, the number of operations required to synthesize the 64 low resolution images may be considerably reduced by 64 times, and the quality of a high resolution image may be ensured.

As described above, according to the examples of the invention, the quality of a generated diagnosis image may be ensured and the number of operations required to generate the diagnosis image may be reduced.

The various elements 108, 110, 120, and 130 in FIGS. 2, 4, and 5 may be implemented using hardware components and/or software components. Software components may be implemented by a processing device, which may be implemented using one or more general-purpose or special-purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purposes of simplicity, the description of a processing device is used as singular; however, one skilled in the art will appreciate that a processing device may include multiple processing elements and multiple types of processing elements. For example, a processing device may include multiple processors or a processor and a controller. In addition, different processing configurations are possible, such a parallel processors.

As used herein, a processing device configured to implement a function A includes a processor programmed to run specific software. In addition, a processing device configured to implement a function A, a function B, and a function C may include configurations, such as, for example, a processor configured to implement functions A, B, and C; a first processor configured to implement function A and a second processor configured to implement functions B and C; a first processor configured to implement functions A and B and a second processor configured to implement function C; a first processor to implement function A, a second processor configured to implement function B, and a third processor configured to implement function C; a first processor configured to implement functions A, B, C and a second processor configured to implement functions A, B, and C, and so on.

The software may include a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion.

In particular, the software and data may be stored by one or more non-transitory computer-readable storage mediums. The non-transitory computer-readable storage medium may include any data storage device that can store data that can be thereafter read by a computer system or processing device. Examples of a non-transitory computer-readable storage medium include read-only memory (ROM), random-access memory (RAM), CD-ROMs, magnetic tapes, floppy disks, and optical data storage devices. Also, functional programs, codes, and code segments for implementing the examples disclosed herein can be easily constructed by programmers skilled in the art to which the examples pertain based on FIGS. 1-7 and their corresponding descriptions as provided herein.

While this invention has been particularly shown and described with reference to various examples, it will be understood by those of ordinary skill in the art that various changes in form and details may be made in these examples without departing from the spirit and the scope of the invention as defined by the claims and their equivalents. The examples should be considered in a descriptive sense only and not for purposes of limitation. Therefore, the scope of the invention is defined not by the detailed description of the invention, but by the claims and their equivalents, and all variations falling within the scope of the claims and their equivalents are to be construed as being included in the invention.

What is claimed is:

1. A diagnosis image generation apparatus comprising:
    a beamforming coefficient calculation unit configured to calculate a beamforming coefficient to be commonly used in forming low resolution images, wherein the beamforming coefficient is calculated using pixel values forming one of the low resolution images;
    a low resolution image synthesis unit configured to synthesize each of the low resolution images using the calculated beamforming coefficient; and
    a high resolution image synthesis unit configured to synthesize a high resolution image using the synthesized low resolution images.

2. The diagnosis image generation apparatus of claim 1, wherein the beamforming coefficient is used in common to calculate a value at a same position in each of the low resolution images among values forming the low resolution images.

3. The diagnosis image generation apparatus of claim 1, wherein the beamforming coefficient calculation unit is further configured to calculate the beamforming coefficient using a minimum variance (MV) beamforming technique for one of the low resolution images.

4. The diagnosis image generation apparatus of claim 3, wherein the one of the low resolution images is one of the low resolution images that corresponds to a signal transmitted from a transducer that transmits the signal first in a transducer array, or a signal transmitted from a transducer that transmits the signal last in the transducer array, or a signal transmitted from a transducer that is located in a middle of the transducer array.

5. The diagnosis image generation apparatus of claim 1, wherein the beamforming coefficient calculation unit is further configured to generate a covariance matrix for values forming the one of the low resolution images;
calculate an inverse of the generated covariance matrix; and
calculate the beamforming coefficient to be commonly used on the low resolution images using the calculated inverse of the covariance matrix.

6. The diagnosis image generation apparatus of claim 1, wherein the beamforming coefficient varies depending on a value indicating a position of a value to which the beamforming coefficient is applied among values forming the low resolution images.

7. The diagnosis image generation apparatus of claim 1, further comprising an adaptive beamformer configured to form a reception beam used to output values forming the low resolution images using the calculated beamforming coefficient.

8. A diagnosis system comprising:
a probe comprising a transducer array, the probe configured to transmit and receive signals to and from a subject; and
a diagnosis image generation apparatus configured to:
synthesize each of low resolution images to which a same beamforming coefficient is applied using signals received from the probe, wherein the beamforming coefficient is calculated using pixel values forming one of the low resolution images;
synthesize a high resolution image using the synthesized low resolution images; and
output the synthesized high resolution image as a diagnosis image.

9. The diagnosis system of claim 8, wherein the beamforming coefficient is commonly used to calculate a value at a same position in each of the low resolution images among values forming the low resolution images.

10. The diagnosis system of claim 8, wherein the diagnosis image generation apparatus is further configured to generate the beamforming coefficient using a minimum variance (MV) beamforming technique for one of the low resolution images.

11. The diagnosis system of claim 8,
wherein one of the low resolution images corresponds to a first transmitted signal from a transducer in the transducer array of the probe, or a last transmitted signal from another transducer of the transducer array, or a middle transmitted signal transmitted from a transducer located in a middle of the transducer array.

12. The diagnosis system of claim 8, wherein the diagnosis image generation apparatus further comprises an adaptive beamformer configured to form a reception beam used to output values forming the low resolution images using the calculated beamforming coefficient as a beamforming weight.

13. A medical image system comprising:
a diagnosis system configured to
synthesize each of low resolution images to which a same beamforming coefficient is applied, wherein the beamforming coefficient is calculated using pixel values forming one of the low resolution images and wherein the low resolution images are formed using signals reflected from a subject;
synthesize a high resolution image using the synthesized low resolution images; and
output the synthesized high resolution image as a diagnosis image; and
a display unit configured to display the output diagnosis image.

14. The medical image system of claim 13, wherein the beamforming coefficient is commonly used to calculate a value at a same position in each of the low resolution images among values forming the low resolution images.

15. A method of generating a diagnosis image, the method comprising:
calculating, using a computer, a beamforming coefficient to be commonly used in forming low resolution images, wherein the beamforming coefficient is calculated using pixel values forming one of the low resolution images and wherein the pixel values are associated with signals received from a subject;
synthesizing, using the computer, each of the low resolution images using the calculated beamforming coefficient; and
synthesizing, using the computer, a high resolution image using the synthesized low resolution images.

16. The method of claim 15, wherein the beamforming coefficient is commonly used to calculate a value at a same position in each of the low resolution images among values forming the low resolution images.

17. The method of claim 15, wherein the calculating of the beamforming coefficient comprises calculating the beamforming coefficient using a minimum variance (MV) technique for one of the low resolution images.

18. The method of claim 17, wherein one of the low resolution images corresponds to a first transmitted signal from a transducer in a transducer array of a probe, or a last transmitted signal from another transducer of a transducer array, or a middle transmitted signal transmitted from a transducer that is located in a middle of the transducer array.

19. The method of claim 15, wherein the calculating of the beamforming coefficient comprises:
generating a covariance matrix for values forming the one of the low resolution images;
calculating an inverse of the generated covariance matrix; and
calculating the beamforming coefficient to be commonly used for the low resolution images using the calculated inverse of the covariance matrix.

20. A non-transitory computer-readable storage medium storing a computer program for controlling a processor to perform the method of claim 15.

21. A method of generating a diagnosis image, the method comprising:
receiving, using a probe, signals corresponding to low resolution images of a subject;
calculating, using a computer, a beamforming coefficient to be commonly used in forming the low resolution images using signals received from the probe corresponding to only one low resolution image of the low resolution images, wherein the beamforming coefficient is calculated using pixel values forming the one of the low resolution images;

synthesizing, using the computer, each of the low resolution images using respective signals for each of the low resolution images in the received signals from the probe and the beamforming coefficient; and synthesizing, using the computer, a high resolution image using the synthesized low resolution images.

22. The method of claim 21, wherein the respective signals corresponding to the low resolution images in the received signals were received at reception points each corresponding to a different one of the low resolution images.

23. The method of claim 21, wherein the synthesizing of each of the low resolution images comprises using the beamforming coefficient to calculate a value at a same position in each of the low resolution images.

24. The method of claim 23, wherein the beamforming coefficient varies according to a position of a value in each of the low resolution images to which the beamforming coefficient is to be applied.

25. The method of claim 21, wherein the calculating of the beamforming coefficient comprises generating a covariance matrix of values for forming the one low resolution image using only the signals corresponding to the one low resolution image;

calculating an inverse of the covariance matrix; and calculating the beamforming coefficient using the inverse of the covariance matrix.

* * * * *